United States Patent [19]

Sanderson et al.

[11] Patent Number: 4,980,514
[45] Date of Patent: Dec. 25, 1990

[54] KETONE DERIVATIVES OF POLYOXYPROPYLENE GLYCOLS

[75] Inventors: John R. Sanderson, Leander; Edward T. Marquis, Austin, both of Tex.

[73] Assignee: Texaco Chemical Company, White Plains, N.Y.

[21] Appl. No.: 444,211

[22] Filed: Dec. 1, 1989

[51] Int. Cl.$^5$ .............................................. C07C 45/29
[52] U.S. Cl. ...................................... 568/405; 568/385
[58] Field of Search ......................... 568/403, 405, 385

[56] References Cited

U.S. PATENT DOCUMENTS 3,479,403 11/1969 MacLean ........................... 568/403
4,225,694 9/1980 Dalton et al. ...................... 568/403
4,609,763 9/1986 Griggs et al. ...................... 568/403

OTHER PUBLICATIONS

Chem. Abst., vol. 96, #142,267y (1982).
Chem. Abst., vol. 77, #23359r (1982).
Sugiyama et al., Chem. Abst., vol. 109, #230,388f (1988).
Barak et al., J. Org. Chem., vol. 53, pp. 3553-35 55 (1988).
Anelli et al., J. Org. Chem., vol. 52, pp. 2559-2562 (1987).

*Primary Examiner*—James H. Reamer
*Attorney, Agent, or Firm*—Jack H. Park; Kenneth R. Priem; Carl G. Ries

[57] ABSTRACT

Diketones useful as intermediates for reaction with carboxylic acids to provide surfactants and for reaction with amine adducts to provide fuel additives are prepared from polyoxyalkylene glycols having a molecular weight of about 200 to about 2,000 and having the formula:

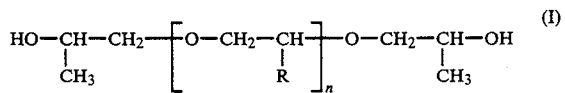

wherein R is hydrogen or methyl and wherein n is a positive number having a value of 1 to about 50, The polyoxyalkylene polyol is oxidized in the presence of a halogenated alkane solvent and a ruthenium catalyst with an alkali metal or alkaline earth metal hypochlorite at a temperature of about 10° to about 50° C. and a pressure of about 0 to 1,000 psig. over a period of about 10 to about 20 hours to provide the corresponding diketone having the formula:

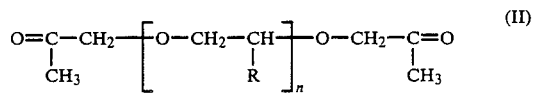

wherein R and n have the meaning given above.

11 Claims, No Drawings

KETONE DERIVATIVES OF POLYOXYPROPYLENE GLYCOLS

BACKGROUND OF THE INVENTION

1. Technical Field of the Invention

This invention relates to the preparation of ketone derivatives of polyoxypropylene glycols. More particularly, this invention relates to a method wherein the terminal hydroxyl groups of a polyoxypropylene glycol are oxidized to ketone groups. Still more particularly, this invention is directed to a method wherein a polyoxypropylene glycol is brought into contact with a hypochlorite oxidant in the presence of a catalytically effective amount of a ruthenium catalyst and a halogenated alkane solvent in order to substantially selectively convert the hydroxyl groups of the polyoxypropylene glycol to terminal ketone groups. The ketone terminated derivatives of polyoxypropylene glycols are useful as intermediates for the preparation of a wide variety of products. For example, they may be reacted with amines to provide fuel additives or converted to carboxylic acids to provide surfactants.

2. Prior Art

It is known to react secondary alcohols and primary benzyl and allyl alcohols to the corresponding ketones and aldehydes in the presence of an oxidant such as Cu(NP$_3$)$_2$ or Zn(NO$_3$)$_2$ supported on silica gel in the presence of an aliphatic hydrocarbon solvent or a chlorinated aliphatic hydrocarbon solvent as shown, for example, by a paper by Takeshi Nishiguchi and Fumi Asano entitled "Oxidation of Alcohols by Metallic Nitrates Supported on Silica Gel" (J. Org. Chem. 1989, 54, 1531–1535).

Willis et al. U. S. Pat. No. 4,233,460 discloses a process for converting alkoxyalkanols to the corresponding acids by reacting the alcohol with an alkali metal hydroxide and a tertiary butyl hydroperoxide in the presence of a catalytic amount of palladium. The oxidation of polyethylene glycols to dicarboxylic acids is disclosed by Morris et al. in U. S. Pat. No. 4,256,916 wherein it is disclosed that polyethylene glycols can be converted to the corresponding carboxylic acids by oxidation in an aqueous solution over a fixed bed of a catalyst consisting of platinum on a granular carbon support.

Stutts et al. U. S. Pat. No. 4,488,944 discloses the preparation of dicarboxylic acids by the oxidation of polyalkylene glycols with electrochemically generated nickeloxide hydroxide.

U. S. Pat. No. 3,479,403 to MacLean discloses that ruthenium can be used as an oxidation catalyst and that activity is enhanced by maintaining the oxidation potential of the ruthenium catalyst at less than the oxidizing potential of Ru(VIII) to greater than that of Ru(IV). In Example I, the oxidation of ethanol to acetic acid by the slow addition of an aqueous solution of calcium hypochlorite to an aqueous solution of ethanol containing a ruthenium chloride catalyst is disclosed. It is also disclosed in this example that the ruthenium chloride was oxidized to ruthenium tetraoxide. The oxidation of isopropanol to acetone with sodium hypochlorite in the presence of a ruthenium trichloride catalyst is also disclosed in Table II of the patent.

Barak et al. in a paper entitled "Selective Oxidation of Alcohols by a H$_2$O$_2$-RuCl$_3$ System under Phase-Transfer Conditions" (J. Org. Chem., 1988, Vol. 53, pp. 3553–3555) discloses in part that secondary alcohols can be oxidized to ketones with one hundred percent selectivity when using hydrogen peroxide as the oxidizing agent. Wolfe et al. disclose in an article entitled "Ruthenium Trichloride-catalysed Hypochlorite Oxidation of Organic Compounds" (Chemical Communications, 1970, pp. 1420–1421) disclose that in the catalytic hypochlorite oxidation of organic compounds with ruthenium trichloride, the ruthenium trichloride is oxidized to ruthenium tetraoxide.

A paper entitled "Fast and Selective Oxidation of Primary Alcohols to Aldehydes or to Carboxylic Acids and of Secondary Alcohols to Ketones Mediated by Oxoammonium Salts under Two-Phase Conditions" by Anelli et al. (J. Org. Chem., 1987, Vol. 52, pp. 2559–2562) discloses oxidation of a variety of alcohols in solution in methylene chloride with sodium hypochlorite.

In all of the prior art references (and in references not cited here) oxidation of polyalkylene glycols has always been on polyethylene glycols. As far as we are aware, there are no references on the oxidation of a polypropylene glycol to diketones. This is especially surprising in view of the fact that lower molecular weight secondary alcohols have been oxidized to ketones.

SUMMARY OF THE INVENTION

In accordance with the present invention, a polyoxyalkylene glycol having a molecular weight of about 200 to about 2,000 and having the formula:

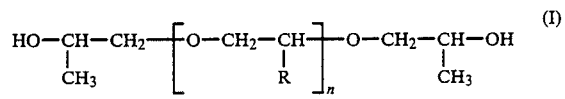

(I)

wherein R is hydrogen or methyl and wherein n is a positive number having a value of 1 to about 50, is oxidized in the presence of a halogenated alkane solvent and a ruthenium catalyst with an alkali metal or alkaline earth metal hypochlorite at a temperature of about 10° to about 50° C. and a pressure of about 0 to 1,000 psig. over a period of about 10 to about 20 hours to provide the corresponding diketone having the formula:

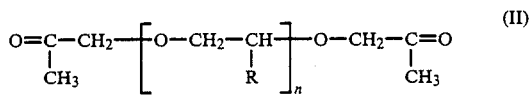

(II)

wherein R and n have the meaning given above.

The thus-prepared diketones are useful as intermediates for conversion to carboxylic acids to provide surfactants and for reaction with amine adducts to provide fuel additives, for example.

In accordance with the preferred embodiment of the present invention, a polyoxypropylene glycol having a molecular weight of about 200 to about 1,000 is added to a reaction zone together with about 4 to about 20 moles per mole of polyoxypropylene glycol of a halogenated methane solvent such as methylene chloride and a catalytically effective amount of a ruthenium oxide catalyst. Thereafter, over a period of about 10 to 20 hours, from about 2 to about 4 moles of an alkali metal hypochlorite oxidant per mole of polyoxypropylene polyol is added at a temperature of about 10 to about 50° C. and a pressure of about 0 to about 500 psig. to substantially quantitatively convert the polyoxypropylene glycol to the corresponding diketone. Still more preferably, the oxidation reaction is conducted in the presence of about 0.5 to about 5 moles of an alkali metal carbonate per mole of hypochlorite oxidant.

DESCRIPTION OF THE PROCESS OF THE PRESENT INVENTION

The starting materials for the present invention include a polyoxyalkylene glycol, as hereinafter defined, a $C_1$-$C_4$ halogenated alkane solvent, a ruthenium catalyst, an alkali metal or alkaline earth metal hypochlorite and, optionally, an alkali metal carbonate.

The ruthenium-containing compounds employed as catalysts may take different forms. For instance, the ruthenium may be added to the reaction mixture in an oxide form, as in the case of, for example, ruthenium (IV) oxide hydrate, anhydrous ruthenium (IV) dioxide and ruthenium (VIII) tetraoxide. Alternatively, it may be added as the salt of a mineral acid, as in the case of ruthenium (III) chloride hydrate, ruthenium (III) bromide, ruthenium (III) iodide, tricarbonylruthenium nitrate, or as the salt of a suitable organic carboxylic acid, for example, ruthenium (III) acetate, ruthenium naphthenate, ruthenium valerate and ruthenium complexes with carbonyl-containing ligands such as ruthenium (III) acetylacetonate. The ruthenium may also be added to the reaction zone as a carbonyl or hydrocarbonyl derivative. Here, suitable examples include, among others, triruthenium dodecacarbonyl and other hydrocarbonyls such as $H_2Ru_2(CO)_{12}$, and substituted carbonyl species such as the tricarbonylruthenium (II) chloride dimer, $(Ru(CO)_3Cl_2)_2$.

Ruthenium-containing compounds include oxides of ruthenium, ruthenium salts of ar organic carbonylic acid and ruthenium carbonyl or hydrocarbonyl derivatives. Among these are ruthenium (IV) dioxide hydrate, ruthenium (VIII) tetraoxide, anhydrous ruthenium (IV) oxide, ruthenium acetate, ruthenium propionate, ruthenium (III) acetylacetonate, and triruthenium dodecacarbonyl.

Additional examples of ruthenium compounds include ruthenium octoate, ruthenium laurate, ruthenium stearate, ruthenium linoleate, ruthenium nitrate, ruthenium sulfate and ruthenium carbonyl.

The polyoxyalkylene glycol feedstock to be used in accordance with the present invention is a polyoxyalkylene glycol having an average molecular weight of about 200 to about 2,000 and having the formula:

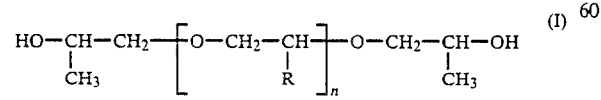

wherein R represents hydrogen or methyl and wherein n is a positive number having a value of 1 to about 50.

A preferred group of polyoxyalkylene glycols to be used as feedstocks are polyoxypropylene glycols having the formula:

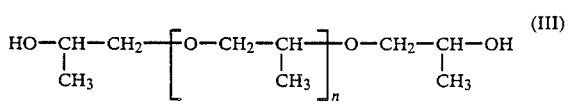

wherein n is a positive integer having a value of 1 to about 40.

Representative products of this nature include, for example, a polyoxypropylene glycol manufactured and sold by Texaco Chemical Company having an average molecular weight of about 230, a polyoxypropylene glycol having an average molecular weight of about 400 sold by the Texaco Chemical Company and a polyoxypropylene glycol having an average molecular weight of about 2,000 sold by the Texaco Chemical Company.

Another group of polyoxyalkylene glycols that can be used to practice the present invention are compounds having the formula:

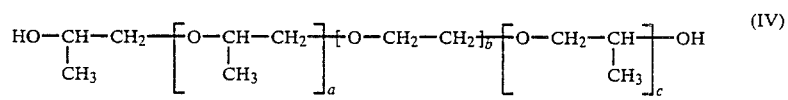

wherein a, b and c are positive numbers and wherein a+c have a value of 2 to about 10 and b has a value of 1 to about 50.

Representative products include a polyoxyethylene/oxypropylene glycol wherein a+c has a value of 2.5 and b has a value of 8.5 and the product has a molecular weight of about 600, a poly(oxyethylene/oxypropylene) glycol having an average molecular weight of about 900 wherein a+c has a value of about 2.5 and b has a value of about 15.5 and a poly(oxypropylene/oxyethylene) glycol having an average molecular weight of about 2,000 wherein a+c has a value of about 2.5 and b has a value of about 40.5.

The solvent to be used should be a halogenated $C_1$-$C_4$ alkane solvent, preferably a halogenated methane such as methylene chloride. However, other solvents may be used such as 1,1,1-trichloroethane, chloroflorocarbons, etc.

The oxidant to be used in accordance with the present invention is an alkali metal or alkaline earth metal hypochlorite such as sodium hypochlorite, calcium hypochlorite, potassium hypochlorite, etc.

The hypochlorite oxidant is preferably employed in the form of 5 to 25 wt.% aqueous solution of the hypochlorite in the ratio of about 2 to about 4;mols of hypochlorite per mole of polyol.

The Reaction Procedure

The reaction procedure to be used in practicing the process of the present invention is a procedure wherein the polyoxyalkylene glycol, the solvent and the ruthenium catalyst are added to a suitable reaction vessel, such as an autoclave, provided with appropriate agitation means and means for controlling temperature within the autoclave such as a jacket through which a heat exchange fluid may be circulated.

About 4 to about 20 moles of solvent should be used per mole of polyoxyalkylene glycol and, more preferably, from about 5 to about 10 moles.

The ruthenium catalyst should be added in a catalytically effective amount. The amount of catalyst to be used with be dependent upon the specific species of ruthenium starting material that is employed. In general, from about 0.0005 to about 0.01 moles of catalyst ganic layer and 50 g concentrated HCl added to the aqueous layer. The aqueous layer was saturated with NaCl and extracted 3×50 ml $CH_2Cl_2$. The $Ch_2Cl_2$ fractions were all combined and dried over anhydrous sodium sulfate. The methylene chloride was then removed on the rotary evaporator and the residue analyzed by IR. Some runs were confirmed by NMR analysis. The results are shown in the attached table.

TABLE I

| | OXIDATION OF POLYPROPYLENE GLYCOL TO KETONE TERMINATED PRODUCT | | | | | | | | | | | |
|---|---|---|---|---|---|---|---|---|---|---|---|---|
| Notebook Number | Polyol | (g) | Catalyst[b] | (g) | Oxidant | (g) | Solvent | (g) | Time (Hr) | Temp (°C.) | % Ketone[a] to Alcohol | Remarks |
| 6446-34 | PPG-230 | 10 | $RuO_2$ | 0.020 | 5% NaOCl | 300 | $CH_2Cl_2$ | 90 | 15 | 38 | 91 | Gentle reflux |
| 6446-51 | PPG-230 | 10 | $RuO_2$ | 0.010 | 5% NaOCl | 300 | $CH_2Cl_2$ | 90 | 15 | 25 | 49 | $H_2O$ bath |
| 6446-52 | PPG-230 | 10 | $RuO_2$ | 0.020 | 5% NaOCl | 300 | $CH_2Cl_2$ | 90 | 15 | 25 | 76 | $H_2O$ bath |
| 6446-53 | PPG-230 | 10 | $RuO_2$ | 0.010 | 5% NaOCl | 300 | None | — | 15 | 25 | 26 | $H_2O$ bath |
| 6446-54 | PPG-230 | 10 | $RuO_2$ | 0.020 | 5% NaOCl | 300 | None | — | 15 | 25 | 34 | $H_2O$ bath |
| 6446-55 | PPG-230 | 10 | $RuO_2$ | 0.010 | 90% TBHP | 20 | $CH_2Cl_2$ | 90 | 15 | 38 | 19 | Gentle reflux |
| 6446-56 | PPG-230 | 10 | $RuO_2$ | 0.020 | 90% TBHP | 20 | $CH_2Cl_2$ | 90 | 15 | 38 | 22 | Gentle reflux |
| 6446-80 | PPG-230 | 10 | None | — | 10% NaOCl | 150 | $CH_2Cl_2$ | 90 | 15 | 38 | 8 | Gentle reflux |
| 6446-87 | PPG-230 | 10 | $RuO_2$ | 0.020 | 10% NaOCl | 300 | $CH_2Cl_2$ | 90 | 15 | 25 | 67 | $H_2O$ bath |
| 6446-88 | PPG-230 | 10 | $RuO_2$ | 0.020 | 10% NaOCl | 300 | $CH_2Cl_2$ | 90 | 16 | 38 | 30 | Gentle reflux |
| 6446-89 | PPG-230 | 10 | $RuO_2$ | 0.10 | 10% NaOCl | 300 | $CH_2Cl_2$ | 90 | 15 | 38 | 92 | Gentle reflux |
| 6446-90 | PPG-230 | 10 | $RuO_2$ | 0.040 | 10% NaOCl | 300 | $CH_2Cl_2$ | 90 | 15 | 38 | 84 | Gentle reflux |
| 6446-91 | PPG-230 | 10 | $Co_3O_4$ | 1.0 | 10% NaOCl | 300 | $CH_2Cl_2$ | 90 | 15 | 38 | 11 | Gentle reflux |
| 6446-92 | PPG-230 | 10 | CuO | 1.0 | 10% NaOCl | 150 | $CH_2Cl_2$ | 90 | 15 | 38 | 11 | Gentle reflux |
| 6446-93 | PPG-230 | 10 | $Fe_3O_4$ | 1.0 | 10% NaOCl | 300 | $CH_2Cl_2$ | 90 | 15 | 38 | 9 | Gentle reflux |
| 6446-94 | PPG-230 | 10 | $Mn_3O_4$ | 1.0 | 10% NaOCl | 300 | $CH_2Cl_2$ | 90 | 15 | 38 | 10 | Gentle reflux |

[a] % ratio of ketone to alcohol determined by IR analysis of reactor effluent.
[b] TBAB = tetrabutylammonium bromide.

should be used per mole of hypochlorite oxidant.

The hypochlorite oxidant is preferably employed in the form of 5 to 25 wt.% aqueous solution of the hypochlorite.

In accordance with the preferred embodiment of the present invention, from about 0.5 to about 5 moles of an alkali metal carbonate, preferably sodium carbonate, is employed per mole of hypochlorite oxidant in order to enhance selectivity.

The reaction should preferably be conducted at a temperature of 10-50° C., at a pressure of 0-1000 psig. and more preferably 0-500 psig., for a time of 10-20 hours and more preferably 10 to 15 hours.

As a result, the polyoxyalkylene glycol feedstock will be substantially selectively converted to the corresponding diketone derivative having the formula:

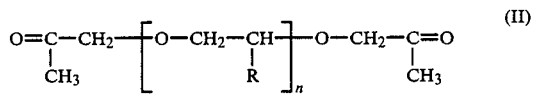

wherein R represents hydrogen or methyl and wherein n is a positive number having a value of 1 to about 50.

SPECIFIC EXAMPLES

The invention will be further illustrated by the following specific examples which are given by way of illustration and not as limitations on the scope of this invention.

Procedure:

Polyol, solvent, and catalyst(s) were charged to a 3-necked flask equipped with stirrer, water bath (or heating mantle) thermometer, water-cooled condenser and addition funnel. The oxidant was added slowly to the stirred reaction mixture over several hours. The reaction mixture was then stirred for an additional 15 hours. The aqueous layer was separated from the or- As will be noted from the results set forth in Table I, the polyoxypropylene feedstock was substantially completely converted to the corresponding diketone in run 6446-34 conducted in accordance with the present invention and in run 6446-89 which is also conducted in accordance with the present invention.

However, when the temperature and the amount of ruthenium catalyst were both reduced in run 6446-51, the conversion to the diketone was only about 50%. Use of an increased amount of catalyst but a lower temperature of 25° C. only resulted in about a 75% conversion to the diketone. In the absences of a solvent (run 6446-53 and 6446-54), the conversions were very poor, ranging from about 25 to about 35%. Use of tertiary butyl hydroperoxide rather than sodium hypochlorite in runs 6446-55 and 6446-56 also resulted in adverse results. Oxidation of the polyoxypropylene glycol in the absence of the ruthenium catalyst in run 6446-80 resulted in only about a 8% conversion to the diketone.

In run 6446-87, when the reaction temperature was only 25° C., there was again a poor conversion to the diketone.

In run 6446-88, where the reaction time was 6 hours, the conversion to the diketone was only 30% whereas in run 6446-89, with a reaction time of 15 hours, the conversion to the diketone was 92%.

The remaining runs in Table I wherein different catalysts such as cobalt, copper oxide, iron and manganese also gave adverse results.

In accordance with the preferred embodiment of the present invention, an alkali metal bicarbonate additive is used to enhance the selectivity to the diketone reaction product.

EXAMPLE 2

Using the procedure of Example 1, a series of experiments were conducted using sodium bicarbonate as an additive. The proportions of the reactants used and the results obtained are summarized in Table II, Table III and Table IV.

TABLE II

| | OXIDATION OF POLYPROPYLENE GLYCOL TO KETONE TERMINATED PRODUCT | | | | | | | | | | | | |
|---|---|---|---|---|---|---|---|---|---|---|---|---|---|
| Notebook Number | Polyol | (g) | Catalyst | (g) | Additive | (g) | Oxidant | (g) | Solvent | (g) | Time (Hr) | Temp (°C.) | % Ketone to Alcohol |
| 6446-35 | PPG-230 | 10 | $RuO_2$ | 0.020 | $NaHCO_3$ | 2.0 | 5% NaOCl | 300 | $CH_2Cl_2$ | 90 | 15 | 38 | 85 |
| 6446-34 | PPG-230 | 10 | $RuO_2$ | 0.020 | — | — | 5% NaOCl | 300 | $CH_2Cl_2$ | 90 | 15 | 38 | 91 |
| 6446-36 | PPG-230 | 10 | — | — | $NaHCO_3$ | 3.0 | 5% NaOCl | 300 | $CH_2Cl_2$ | 90 | 15 | 38 | 13 |
| 6446-37 | PPG-230 | 10 | — | — | $NaHCO_3$ | 3.0 | 5% NaOCl | 300 | $CH_2Cl_2$ | 90 | 15 | 25 | 18 |
| 6446-38 | PPG-230 | 10 | — | — | NaOH | 4.0 | 5% NaOCl | 300 | — | — | 15 | 25 | 14 |
| 6446-41 | PPG-230 | 10 | $RuO_2$ | 0.010 | NaOH | 4.0 | 5% NaOCl | 300 | $CH_2Cl_2$ | 90 | 15 | 25 | 5 |
| 6446-84 | PPG-230 | 10 | — | — | — | — | 10% NaOCl | 150 | $CH_2Cl_2$ | 90 | 15 | 38 | 2 |

TABLE III

| RELATIVE MOL. % TERMINATION BY C-13 NMR | | |
|---|---|---|
| | Ketone | Alcohol |
| 6446-34 | 91 | 9 |
| 6446-35 | 85 | 15 |

TABLE IV

| PERCENTAGE OF TOTAL CARBON AREA BY C-13 NMR | | | |
|---|---|---|---|
| | Ketone | Other Carbonyl | Olefin |
| 6446-34 | 5.4 | 1.2 | 0.6 |
| 6446-35 | 4.6 | <0.2 | 0.3 |

The explanation of the results obtained in run 6446-35 as compared with run 6446-34 is as follows.

With respect to Table II, 6446-35 and 6446-34 are identical except that $NaHCO_3$ has been added to 6446-35. The conversion (as measured by IR) is actually slightly less than the run in the absence of $NaHCO_3$. At first glance, then, $NaHCO_3$ appears to be slightly detrimental. However, IR analysis measures only the conversion and not the selectivity.

Table III shows the relative mole % termination by C-13 NMR. Agreement is excellent with the results obtained by IR. Table IV shows the percentage of total carbon area by C-13 NMR. It is here that we see the superior results obtained in the presence of $NaHCO_3$ Note that olefin byproduct has been cut in half and other carbonyl by-products have been reduced by more than a factor of 6 !

Experiment 6446-41 done in the presence of NaOH and $RuO_2$ showed only 5% conversion. $NaHCO_3$ alone (6446-36, 37) and NaOH alone also showed poor results.

The foregoing examples have been given by way of illustration only, and are not intended as limitations on the scope of this invention, which is defined by the following claims.

We claim:

1. A method of making a diketone having the formula:

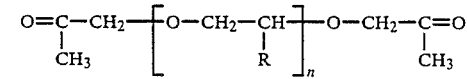

(II)

which comprises adding to a reaction zone a $C_1$-$C_4$ halogenated alkane solvent, a ruthenium catalyst and a polyoxyalkylene glycol having an average molecular weight of about 200 to about 2,000 and having the formula:

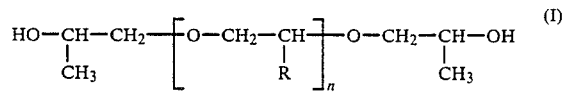

(I)

then continuously adding an aqueous solution of an alkali metal or an alkaline earth metal hypochlorite oxidant to the reaction mixture with agitation at a temperature of about 10° to about 50° C. and a pressure of about 0 to 1,000 psig. over a period of about 10 to 20 hours, whereby said polyoxyalklene glycol will be substantially selectively converted to said corresponding diketone, and recovering said diketone derivative, wherein R in said formulas represents hydrogen or methyl and wherein n is a positive number having a value of 1 to about 50.

2. A method as in claim 1 wherein the polyoxyalkylene glycol is a polyoxypropylene diol having the formula:

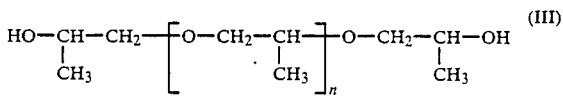

(III)

wherein n is a positive number having a value of 1 to about 40.

3. A method as in claim 1 wherein the polyoxyalkylene glycol is a diol having the formula:

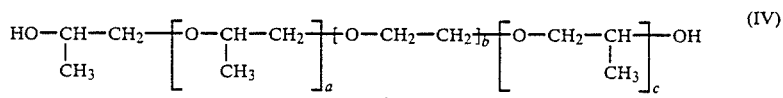

(IV)

wherein a+c equals a positive number having a value of 2 to about 10 and b is a positive number having a value of 1 to 50.

4. A method as in claim 1 wherein the reaction is carried out in the presence of an alkali metal bicarbonate.

5. A catalyzed hypochlorite oxidation method for making a diketone derivative having the formula:

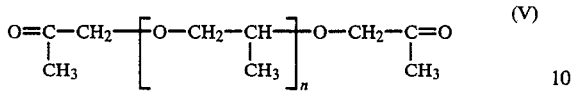 (V)

which comprises adding to a reaction zone a polyoxypropylene glycol, from about 4 to about 20 mols, per mole of polyoxypropylene glycol of a halogenated methane solvent, an alkali metal carbonate and a catalytically effective amount of a ruthenium oxide catalyst, then continuously adding an alkali metal hypochlorite oxidant as about a 5 wt.% to about a 25 wt.% aqueous solution to the reaction mixture with agitation at a molar ratio of about 2 to 4 moles of hypochlorite per mol of polyol at a temperature of about 10° to about 50° C. and a pressure of about 0 to 500 psig. over a period of about 10 to 20 hours, whereby said polyoxypropylene glycol feedstock will be substantially selectively converted to said diketone derivative, and recovering said diketone derivative, said alkali metal carbonate being initially added to said reaction zone in an amount ranging from about 0.5 to about 5 mols of an alkali metal bicarbonate per mol of said hypochlorite, said polyoxypropylene glycol having an average molecular weight of about 200 to about 1,000 and having the formula:

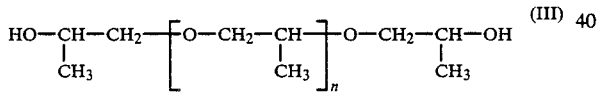 (III)

wherein n is a positive number having a value of 1 to about 40.

6. A method as in claim 5 wherein the hypochlorite is sodium hypochlorite.

7. A method as in claim 6 wherein the halogenated methane is methylene chloride.

8. A method as in claim 7 wherein the alkali metal bicarbonate is sodium bicarbonate.

9. A method of making a diketone having the formula:

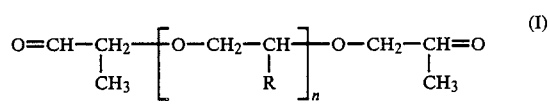 (I)

wherein R represents hydrogen or methyl and wherein n is a positive number having a value of 1 to about 50, which comprises adding to a reaction zone a polyoxyalkylene glycol having an average molecular weight of about 200 to about 2,000 and having the formula:

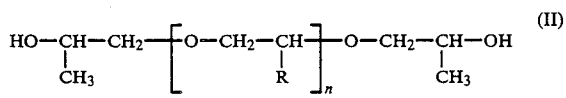 (II)

wherein R and n have the meaning given above, said polyoxyalkylene glycol being added to said reactor in solution in from about 4 to about 20 moles of a halogenated $C_1$–$C_4$ alkane solvent together with a ruthenium oxide catalyst and then continuously adding a 5 to 25 wt.% aqueous solution of an alkali metal or an alkaline earth metal hypochlorite oxidant to the reaction mixture in an amount within the range of about 2 to about 4 moles of said hypochlorite per mole of said glycol with agitation at a temperature of about 10° to about 50° C. and at a pressure of about 0 to 1,000 psig. over a period of about 10 to 20 hours, whereby said polyoxyalklene glycol will be substantially selectively converted to said corresponding diketone derivative, and recovering said diketone derivative, from about 0.0005 to about 0.1 moles of said ruthenium oxide catalyst being used per mole of said hypochlorite.

10. A method as in claim 9 wherein the reaction is carried out in the presence of about 0.5 to 5 moles of an alkali metal carbonate per mole of hypochlorite.

11. A method as in claim 10 wherein the alkali metal carbonate is sodium bicarbonate.

* * * * *